(12) United States Patent
Beoni

(10) Patent No.: US 8,221,497 B2
(45) Date of Patent: Jul. 17, 2012

(54) MIDDLE EAR PROSTHETIC DEVICE

(76) Inventor: Franco Beoni, Piacenza (IT)

(*) Notice: Subject to any disclaimer, the term of this patent is extended or adjusted under 35 U.S.C. 154(b) by 307 days.

(21) Appl. No.: 12/572,714

(22) Filed: Oct. 2, 2009

(65) Prior Publication Data

US 2011/0066240 A1    Mar. 17, 2011

(30) Foreign Application Priority Data

Sep. 14, 2009  (EP) .................... 09170237

(51) Int. Cl.
*A61F 2/18* (2006.01)
(52) U.S. Cl. .......................................... 623/10
(58) Field of Classification Search ........... 623/10; 600/25
See application file for complete search history.

(56) References Cited

U.S. PATENT DOCUMENTS

| | | | | |
|---|---|---|---|---|
| 3,824,629 A | * | 7/1974 | Shiley | 623/2.25 |
| 3,909,852 A | * | 10/1975 | Homsy | 623/10 |
| 5,941,814 A | * | 8/1999 | Lehner et al. | 600/25 |
| 2008/0195201 A1 | | 8/2008 | Steinhardt et al. | |
| 2008/0234817 A1 | * | 9/2008 | Huettenbrink et al. | 623/10 |

FOREIGN PATENT DOCUMENTS

DE  10 2007 013 708 B3  1/2008
EP       0 460 354 A2   12/1991

* cited by examiner

*Primary Examiner* — Thomas J Sweet
*Assistant Examiner* — Yashita Sharma
(74) *Attorney, Agent, or Firm* — Oblon, Spivak, McClelland, Maier & Neustadt, L.L.P.

(57) ABSTRACT

The middle ear prosthetic device comprises: a columellate prosthesis arranged to replace the ossicular chain of the middle ear with the exception of the stapes footplate or the entire stapes, a first end of this prosthesis being intended to be inserted into a hole provided in the footplate or to rest on the footplate itself, or to be connected to the stapes capitellum respectively; an annular element of bioinert metal insertable into the auditory tube at the position in which the neotympanum is to be formed; a tensostructure of non-reabsorbable bioinert material, which extends into the interior of the annular element and is fixed to this latter, the tensostructure presenting apertures which provide the surgeon with a sufficient view of the surgical field and allow the required surgical manoeuvres; first and second means for connecting the second end of the columellate prosthesis and the neotympanum to the tensostructure respectively.

18 Claims, 4 Drawing Sheets

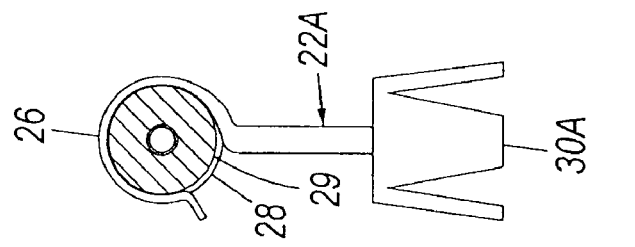
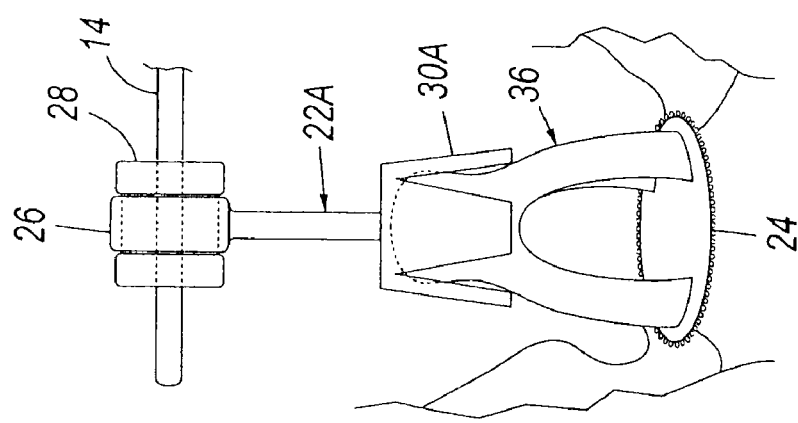
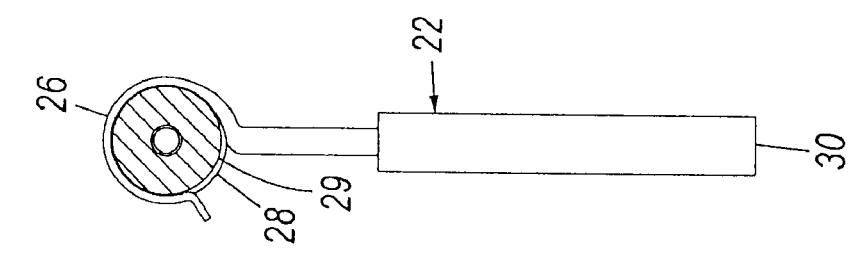
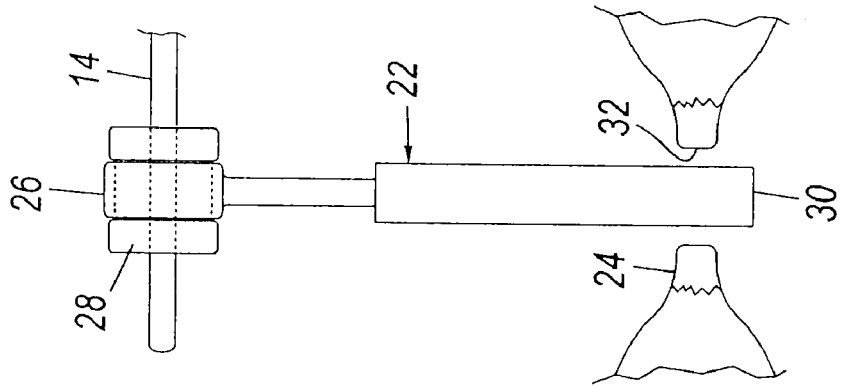

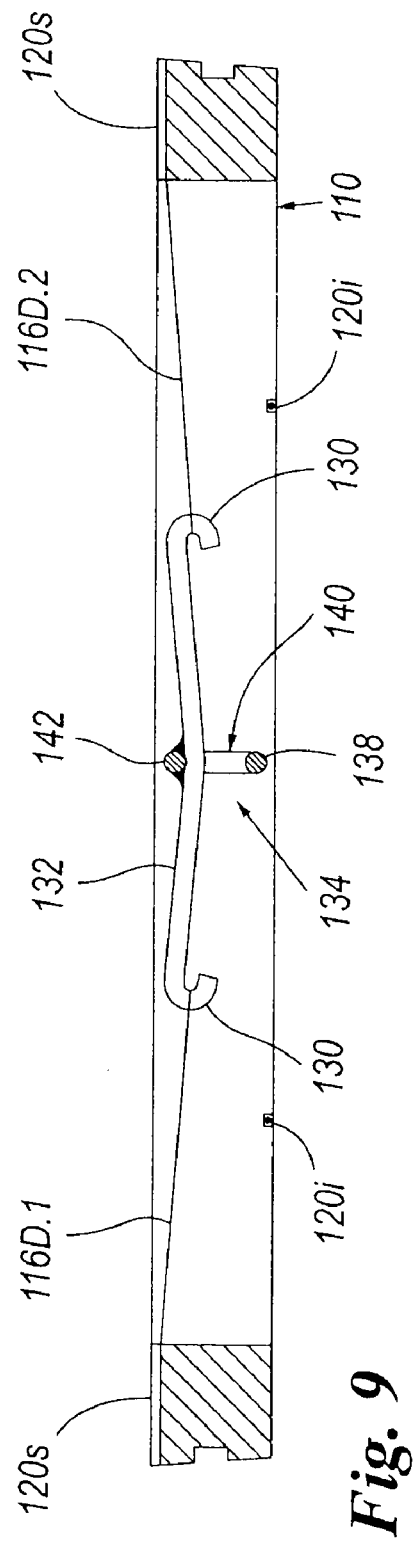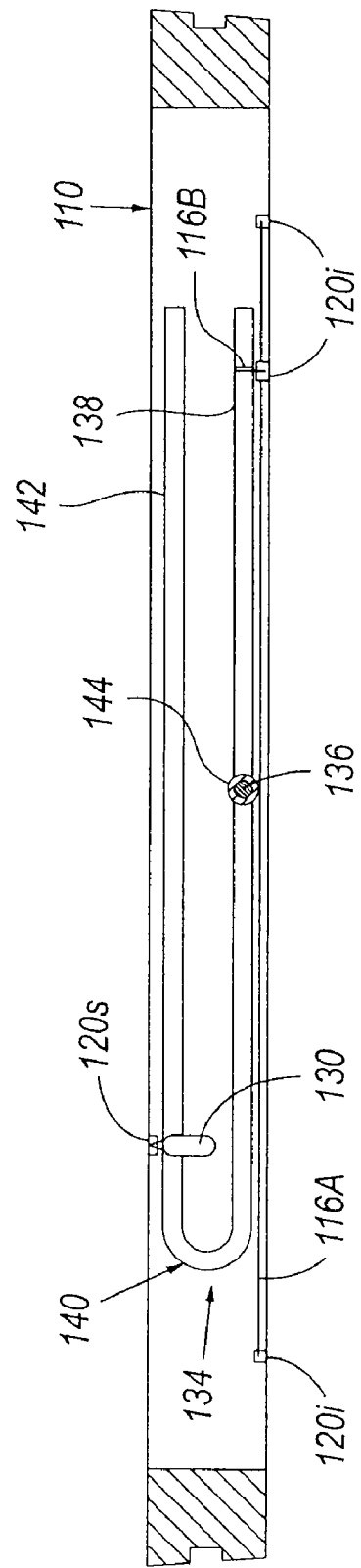

MIDDLE EAR PROSTHETIC DEVICE

The present invention relates to a middle ear prosthetic device.

As known to the expert of the art, reconstructive interventions on the middle ear must take into account two different starting situations:

1. The tympanum is lacking but the ossicular chain is intact: only the tympanum is reconstructed, using tissue of the actual patient (autologous neotympanum). The neotympanum is assembled such as to come into contact with the hammer handle of the integral ossicular chain, to form a continuity in sound wave transmission. The intervention has a success rate of about 90%.

2. The tympanum and the ossicular chain are lacking: the tympanum is reconstructed as in situation 1 (without contacting the missing hammer handle) and the ossicular chain is replaced by a heteroplastic ossicular prosthesis or, if possible, by a prosthesis of autologous material. Even though during recent decades many ossicular prosthesis models have been conceived using various biomaterials, the functional results of an intervention starting from situation 2 have only slightly improved. It has now been realized that the intervention presents a high percentage of functional failure because of post-operative displacement of the ossicular prosthesis, also known as a columellate prosthesis. This prosthesis is subjected to forces such as gravity and pressure variations within the tympanic box (in particular due to sneezing, and variations in altitude and underwater depth). The displacement of the columellate prosthesis is in practice inevitable as its part facing outwards is not fixed to the neotympanum. Moreover, even if the prosthesis has not yet shifted, it does not allow good sound wave transmission as its end facing inwards simply rests on the stapes ossicle, with little transmission power. Sound wave transmission could be optimized if said end of the prosthesis could dip into a hole provided in the stapes footplate, as in the stapedotomy intervention for otosclerosis. However this solution cannot be applied in our case because (as already stated) at its other end the ossicular prosthesis is not fixed to the neotympanum, so that it would sink into the inner ear through said footplate hole, causing irreversible damage to the cochlea of the acoustic nerve.

A middle ear prosthetic device is already known, comprising:

a columellate prosthesis arranged to replace, in sound wave transmission, the ossicular chain of the middle ear, one end of this prosthesis being intended to be inserted into a hole provided in the footplate or more easily but with poorer sound transmission results to be connected to the footplate itself, or to be connected to the stapes;

an annular element of bioinert metal insertable, by previous milling, into the auditory tube at the position in which the neotympanum is to be formed;

an elastic elongated element of bioinert metal, a first end of the elongated element being rigid with the annular element while its second end is free, at or in the vicinity of this second end there being connected the other end of the columellate prosthesis;

for supporting the neotympanum, a tensostructure of wires of non-reabsorbable bioinert material, which extends into the interior of the annular element and is fixed to this latter, the distance between the wires being such as to provide the surgeon with a sufficient view of the surgical field and allow the required surgical manoeuvres, the elongated elastic element interfering with the tensostructure.

In particular, the wires of the tensostructure are surgical wires of bioinert polymer, the elongated elastic element being a piece of nitinol wire of the so-called superelastic type.

An embodiment of this known prosthetic device is illustrated in FIGS. 1 to 7.

With reference to said figures, the annular element 10 of said prosthetic device is intended to be located by the surgeon in the patient's auditory tube 38 (FIG. 3), after reaming by surgical millers to enable it to be inserted in position. The annular element 10 is of a bioinert metal (for example titanium ASTM F67, group 2) and presents in its outer edge an annular groove 12 enabling bone tissue to re-grow within it, so preventing movement of the annular element 10.

As can be seen from FIGS. 1-3, an elongated elastic element 14 extends diametrically from the inner side of the annular element 10 and has a corresponding end fixed into the annular element 10 while its other end is free. The elongated element 14 is preferably of nitinol superelastic (for example that produced by Nitinol Devices & Components, California, USA).

A tensostructure, indicated overall by 15, formed from a weave of wires 16A and 16B is fixed taut to the annular element 10 for the purpose of supporting the neotympanum 18 reconstructed from tissue of the actual patient by a classical surgical technique. The wires 16A and 16B are preferably of the non-reabsorbable type used for surgical sutures. The ends of the wires 16A and 16B are inserted into relative recesses, 20A and 20B respectively, provided in the annular element 10, and are locked in these recesses by deformation (not shown for simplicity) of the metal surrounding the individual recess. A recess 20C is also provided for receiving that end of the elongated element 14 intended to be fixed into the annular element 10. This fixing is again conveniently achieved by deformation (again not shown) of the metal surrounding the recess 20C. The elongated element 14 rests on the wires 16A so that the neotympanum 18 rests thereon as well.

As can be seen from FIG. 1, about the free end of the elongated elastic element 14 there is wound a wire 16C the two ends of which are inserted into respective recesses 20D in which these ends are locked, again by deformation of the adjacent metal of the annular element 10, taking care that the wire 16C is under tension, hence forming a means for retaining the elongated elastic element 14 in its non-deformed condition until to the free end of this latter a columellate prosthesis 22 has been coupled (FIGS. 4 and 5) if only the stapes footplate 24 remains or has been maintained and bored, whereas a prosthesis 22A is coupled (FIGS. 6 and 7) if the entire stapes 36 is present and is to be maintained, this prosthesis being provided with an end 30A shaped to be mounted over the capitellum of the stapes 36, as shown in FIG. 6.

The hook-shaped end of the prosthesis 22 or 22A (FIGS. 4-7) is deformable to be able to embrace the elongated element 14, to prevent accidental unhooking. The same object can be conveniently attained by making this hook-shape end of elastic material, to enable it to be snap-coupled to the elongated element 14.

The annular element 10 is conveniently formed with an outer conicity of 2° and has an outer diameter ranging from 8.0 to 13.0 mm, by preferably providing an entire series of annular elements with their outer diameter differing by 0.5 mm, to adapt to different patients.

It has however been found that the aforedescribed prosthetic device presents certain drawbacks. In this respect it has been found that neotympanum 18, reconstructed by autotransplant (e.g. using the temporal muscle fascia of the patient), and which rests on the tensostructure 15 and hence also on the elongated element 14, retracts during its bedding-in, to rise within the external auditory tube and hence lose contact with the elongated element 14. The result is that following cicatrized retraction of the neotympanum 18, sound wave transmission from the tympanum to the elongated element 14 gradually reduces during a period of 3-6 months from the operation, to reach zero if the retraction is such as to make the tympanum 18 lose contact with the elongated element 14.

Moreover, to obtain good results the prosthesis 22 or 22A is coupled in the vicinity of the free end of the elongated element 14, where the amplitude of the vibrations of the elongated element 14 is greatest. If the columellate prosthesis were coupled in a different position, transmission would be increasingly less the greater the distance from the free end of the elongated element 14. It should also be noted that as the elongated element 14 is fixed into the annular element 10, the elongated element 14 vibrates only if the neotympanum 18 transmits sufficient energy to it.

The object of the present invention is to provide a middle ear prosthetic device which does not present the aforespecified drawbacks. This object is attained by a middle ear prosthetic device according to the present invention, comprising:

a columellate prosthesis arranged to replace, in sound wave transmission, the ossicular chain of the middle ear with the exception of the stapes footplate or the entire stapes, a first end of this prosthesis being intended to be inserted into a hole provided in the footplate or to rest on the footplate itself, or to be connected to the stapes capitellum;

an annular element of bioinert metal insertable, by previous milling, into the auditory tube at the position in which the neotympanum is to be formed;

a tensostructure of non-reabsorbable bioinert material, which extends into the interior of the annular element and is fixed to this latter, the tensostructure presenting apertures which provide the surgeon with a sufficient view of the surgical field and allow the required surgical manoeuvres;

first means for connecting the second end of the columellate prosthesis to the tensostructure;

second means for connecting the neotympanum to the tensostructure.

Said first means can for example comprise, fixed to the tensostructure, a first arm to which the second end of the columellate prosthesis can be connected to thus establish a connection between the columellate prosthesis and the tensostructure. This is particularly simple if the second end of the prosthesis is shaped as a hook, this latter being fixable to the first arm by deformation of the hook itself or conveniently making the hook of elastic material, which enables it to be snap-coupled to said first arm.

Said second means can for example comprise a second arm fixed to the tensostructure, this second arm being insertable into a hole provided in the neotympanum in a position enabling this to be achieved, to thus allow the neotympanum to grasp the tensostructure.

The first arm and second arm can conveniently form part of the same element fixed to the tensostructure.

The tensostructure can conveniently be of the type comprising wires, in particular surgical wires of a non-reabsorbable bioinert polymer, in particular to form a type of mesh. It should however be noted that the tensostructure could also be of the membrane type provided with apertures of suitable dimensions and number to provide the surgeon with a sufficient view of the surgical field and allow the required surgical manoeuvres.

To avoid confusion, that end of the columellate prosthesis to be connected to said first arm, located close to the tympanum, will be known as the outer end, the other end being known as the inner end.

Also in the case of the prosthesic device of the present invention, if only the stapes footplate remains, the columellate prosthesis is provided with an inner end shaped to be inserted into a hole previously provided (as in FIGS. 4 and 5) in the footplate, or to rest on this latter if said hole is not provided in the footplate.

If however the entire stapes is still present and it has been decided, for particular reasons, to let it remain, a columellate prosthesis can be used, the inner end of which is shaped in such a manner (for example as a cap, such as that of FIGS. 6 and 7) as to be able to be mounted on the stapes capitellum.

By virtue of the prosthetic device of the present invention, correct positioning of one of the two aforesaid types of columellate prosthesis can be achieved without particular difficulty by the surgeon, who can visually verify it.

The invention will be more apparent from the ensuing description of one embodiment thereof provided by way of example. In this description reference is made to the accompanying drawings, in which:

FIG. 4 shows on an even more enlarged scale a columellate prosthesis forming part of the prosthetic device, of the type suitable for the case in which a hole in the stapes footplate is formed;

FIG. 5 shows the same, and the one alone, prosthesis rotated through 90°;

FIG. 6 shows instead a columellate prosthesis of the type suitable for the case in which the entire stapes is still present;

FIG. 7 shows the latter prosthesis, and the one alone, rotated through 90°;

FIG. 9 is a more enlarged cross-section therethrough on the line 9-9 of FIG. 8;

FIG. 10 is a cross-section therethrough on the same scale as FIG. 9, taken on the line 10-10 of FIG. 8.

Figure 8:
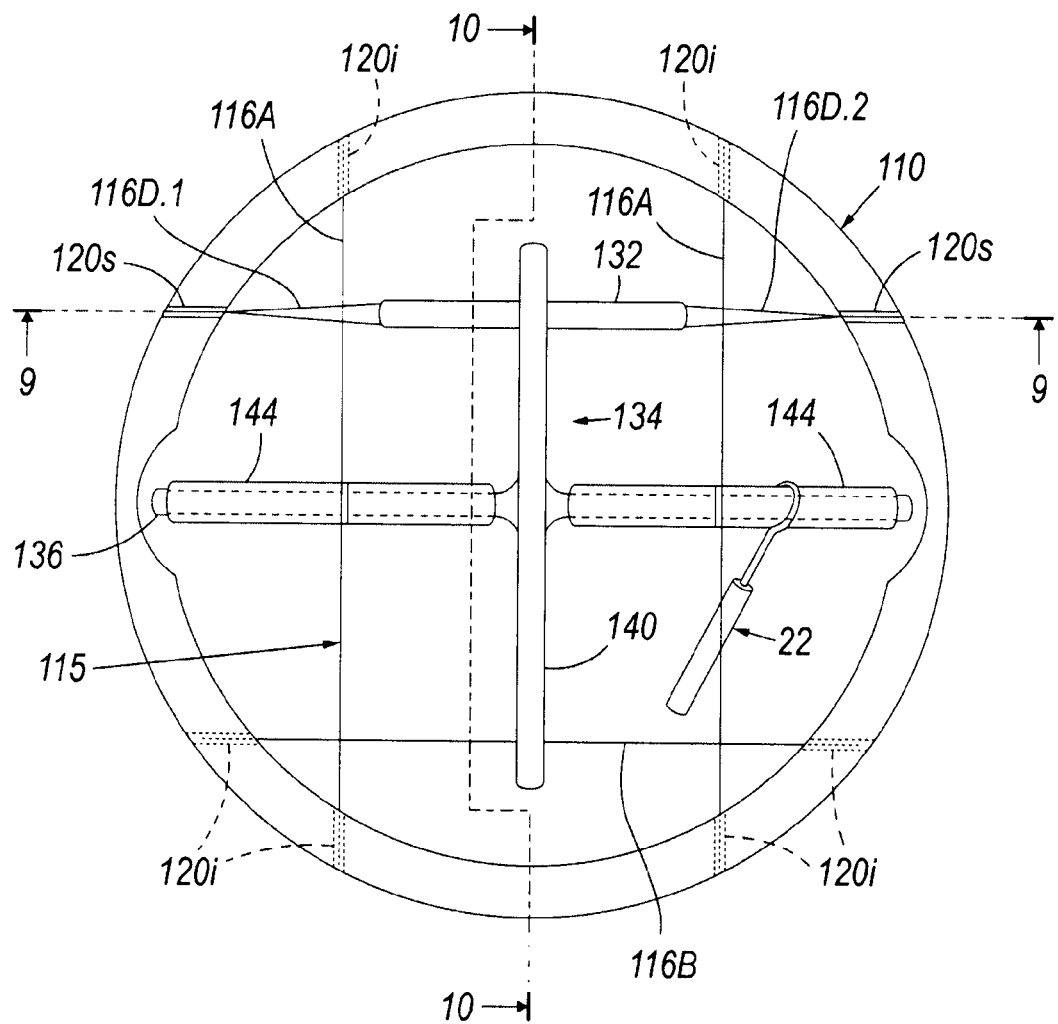
FIG. 8 is a plan view, enlarged compared with reality, of a middle ear prosthetic device according to the invention.

Before describing these figures, it should be noted that the columellate prosthesis 22 shown schematically in FIG. 8 is in this specific case identical to that of FIGS. 4 and 5, also indicated by 22. From the aforegoing it is also apparent that in FIG. 8 the columellate prosthesis 22A of FIGS. 6 and 7 can replace the prosthesis 22.

As to the remaining elements, hereinafter, elements equal or similar to those of the known prosthetic devices of FIGS. 1-7 are indicated by the same reference numbers plus 100.

Figure 1:
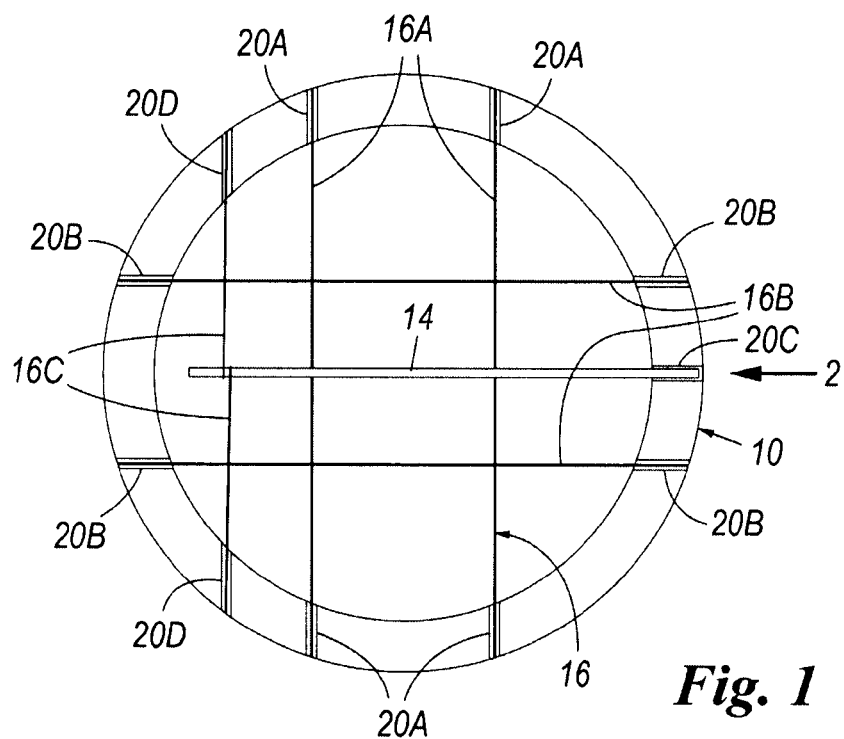
FIG. 1 is a view from above of said annular element with relative elongated elastic element (some dimensions being shown greater than reality for clarity)
Figure 2:
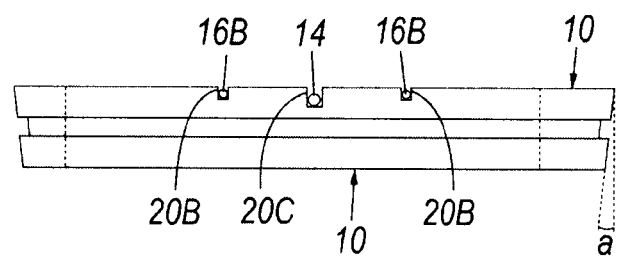
FIG. 2 is a view thereof in the direction of the arrow 2 of FIG. 1.
Figure 3:
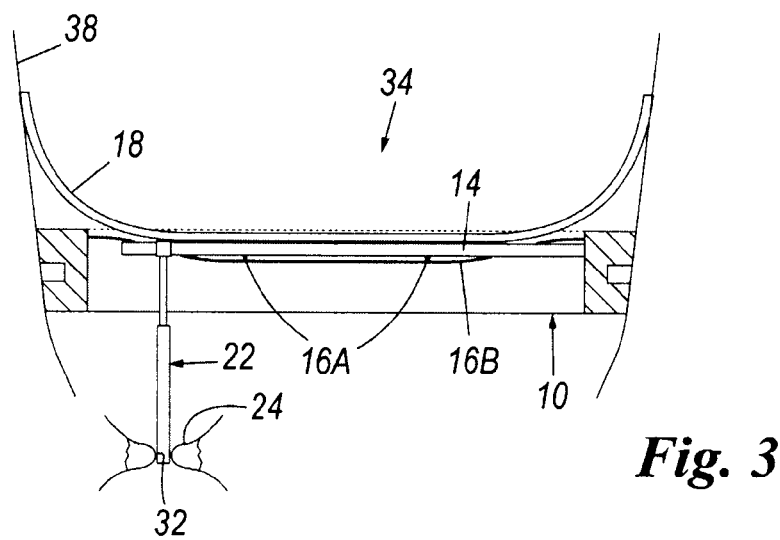
FIG. 3 is a very schematic section through part of the auditory tube and of the relative tympanic box after said prosthetic device has been implanted by surgical intervention (in the figure some dimensions have been altered for clarity)

Returning to FIGS. 8-10, these show an annular element 110 which, in the same manner as the annular element of FIGS. 1-3, is intended to be located by the surgeon within the auditory tube of the patient after milling by a special miller provided with the prosthesic device, to enable the annular element 110 to be inserted in position. This latter is of a bioinert metal (for example titanium ASTM F67, group 2) and presents in its outer edge an annular groove 112 within which bone tissue re-grows over time, so preventing movement of the annular element 110.

As can be seen from FIGS. 8-10, a tensostructure indicated overall by 115 is present inside the annular element 110 and is fixed taut thereto. In the specific illustrated case, the tensostructure 115 is formed from four taut wires, specifically two substantially parallel wires 116A disposed symmetrically, a wire 116B substantially coplanar with the wires 116A but substantially perpendicular thereto, and a wire 116D substantially parallel to the wire 116B and formed in this specific case by two opposing wire portions 116D.1 and 116D.2 which leave from respective recesses 120 provided on the lower face of the annular element 110 to pass through corresponding hooks 130 (FIG. 9) and then return to the relative recess 120. The hooks 130 are provided at each of the two ends of the shorter crosspiece 132 of a connection element, indicated overall by 134, shaped roughly as a Lorraine cross (see FIG. 8). The two ends of each wire portion 116D.1 and 116D.2 are confined taut within the relative recess 120 by deformation of the surrounding metal of the annular element 110. The ends of the other wires 116A and 116B are confined taut in the same manner within similar recesses 120 provided in the lower face of the annular element 110. In particular, the wires 116A pass about the relative arm 144 of the longer crosspiece 136 of the connection element 134. The upright 140 of the Lorraine cross has an elongated U-shape, disposed prone (FIG. 10), so that it lies in a diametrical plane of the annular element 110. In turn, the wire 116B passes about the lower or inner arm 138 (FIG. 10) of the upright 140.

The tensostructure 115 supports the connection element 134 of Lorraine cross shape, which is formed of a bioinert metal (conveniently the same metal as the annular element 110). The connection element 134 performs in this specific case the function both of the aforesaid first connection means and of the aforesaid second connection means. In this respect, the aforementioned first arm is nothing other than one of the two opposing arms of the longer crosspiece 136 of the connection element 134, to one of which arms the aforesaid columellate prosthesis 22 (FIGS. 8, 4 and 5) or 22A (FIGS. 6 and 7) can be coupled, depending on the situation. To prevent the columellate prosthesis 22 or 22A from being able to accidentally become uncouple, a PTFE sleeve 144 is mounted on each of the two arms of the longer crosspiece 136 to achieve this result.

In its turn, the upper or outer arm 142 of the U-shaped upright 140 is nothing other than the aforesaid second arm, to be inserted into said hole appropriately provided in the neotympanum (as already stated and as further explained hereinafter). This enables the required connection to be established between the tensostructure 115 and the neotympanum (similar to the neotympanum indicated by 18 in FIG. 3).

Consequently the connection element 134 of Lorraine cross shape performs the function both of the aforesaid first connection means and of the aforesaid second connection means.

The wires 116A, 116B and 116D of the tensostructure 115 are again preferably of the non-reabsorbable type, used for surgical sutures.

As in the case of the annular element 10 of FIGS. 1-3, the annular element 110 is also conveniently made with an outer conicity (for example of 2°) and an outer diameter from 8.0 to 13.0 mm, such that the surgeon has available an entire range of these elements of different diameter, from which to choose that most suitable for a determined patient (for exampled a series of annular elements of outer diameter differing by 0.5 mm). The cross-section of the annular element 10 can for example have a height of 1.0 mm and a width of 0.6 mm.

With regard to the Lorraine cross-shaped connection element 134, this can for example be made from pieces of titanium wire of 0.2 mm diameter, welded together.

The distance between the outer arm 142 and the inner arm 138 of the U upright 140 allows to insert a leaf, suitably shaped, of (autologus) cartilage, so that the neotympanum does not contact with the titanium and the PTFE of the cross 134, to this end also the outer arm 142 (protruding over the neotympanum) being lined with a length of vein taken from the patient's hand, put on the outer arm 142.

A brief description will now be given of how the middle ear prosthetic device of the present invention is applied to the patient.

The surgeon firstly executes the classical surgical steps of tympanoplasty, to amply expose the outer auditory tube, which is rounded with conventional surgical millers, then completing reaming with frusto-conical diamond-clad millers (see EP-B-0460354). To construct the neotympanum, autologus tissue (such us the temporal muscle fascia of the patient) is taken. This tissue is extended on a model of the outer auditory tube reamed, so that it can dry up, assuming the shape of the model.

Conveniently, a series of such models, with diameter of 8.0-13.0 mm (like for the annular elements 110), is prepared in advance, which models can be supplied to the surgeon as accessories of the prosthesic devices of the present invention.

At this point the annular element 110 already provided with the tensostructure 11 carrying the connection element 134 is inserted into position. The annular element 110, having its outer surface frusto-conical, is fixed into its seal, possibly with the aid of metal wedges forcibly inserted between the annular element 110 and the reamed auditory tube (also said wedges can be supplied to the surgeon as accessories of the prosthesic devices of the invention).

The distance is then measured between the arm of the longer crosspiece 136 to which the columellate prosthesis 22 is to be coupled, and the stapes footplate (if only the footplate of the stapes remains or has been retained), or the distance between said arm and the stapes capitellum (if this latter is totally present and it has been decided to integrally retain it) such as to be able to choose that columellate prosthesis (available in various sizes) of one of the two said types (22, 22A) having a length suitable for the specific case. If only the stapes footplate remains or is retained, platinotomy (holing the footplate) is effected in conventional manner (for example by diode or CO2 laser), the hole 32 (FIG. 4) having a diameter suitable for receiving the shank 30 of the prosthesis 22, as in the know technique in interventions for stapedotomy for otosclerosis.

At this point, the patient's temporal muscle fascia is used previously extended on the aforementioned model to dry. The dried tissue maintains the model shape, this making the insertion thereof easy at the time of the surgical operation (as in the tympanoplasty, where the dried neotympanum is connected to the hammer handle of the human ossicular chain).

A hole is formed in a suitable position of the obtained neotympanum having the same diameter as the outer arm 142 (FIG. 10) of the U-shaped upright 140 (for example having a diameter of 0.2 mm). The neotympanum is now adapted to the tensostructure 115 by inserting the outer arm 142 of the upright 140 into the hole formed in the neotympanum, substantially in the manner in which the hammer handle is inserted into this hole in the case of tympanoplasty. The outer arm 142 then lies above the neotympanum and is then covered (as already mentioned) using a small vein of the patient, mounted in the manner of a sleeve about the outer arm 142.

The neotympanum is now spread not only onto the tensostructure 115 but also onto the previously reamed adjacent walls of the auditory tube, except for a part (upper rear quadrant) so as to be able to insert the columellate prosthesis 22 or 22A into position by fixing the relative hook (by snap fitting if it is resilient or, if not, by deformation thereof) to one of the two arms 144 of the longer crosspiece 136 of the connection element 134. A leaflet of cartilage previously taken from the patient and reduced to dimensions such as to cover the Lorraine cross-shape element 134, inserting said leaflet between the two arms 138 and 142 of the latter, so as to prevent contact of the neotympanum with titanium and PTFE (it is know that such a contact can cause perforation of the neotympanum).

The neotympanum is further spread to cover the tympanic area and the adjacent walls of the reamed auditory tube. The neotympanum is then fixed with fibrin glue, covering it peripherally with the residual skin tabs of the tube, in accordance with the classical tympanoplasty technique. The auditory tube is medicated with an elastic band of medical silicone which holds the skin tabs and the peripheral part of the neotympanum against the walls of the auditory tube, then finally filling this latter with reabsorbable sponge, according to the known art.

It should be noted that in some cases it could be necessary or convenient to replace the stapes footplate (indicated by 24 in FIG. 6) with a tab of tissue from the patient (for example a vein tab).

If the entire stapes is still present and for some reason it is to be retained integrally, a columellate prosthesis 22A can be used with a cap-shaped lower end (indicated by 30A in FIGS. 6 and 7), to be mounted over the capitellum of the stapes 36. To a surgeon expert in the art, it is evident how the surgical procedure must be varied to adapt it to this type of prosthesis, hence no further description will be given. The decision could also be taken, if desired, not to implement the platinotomy, but simply to rest the inner end 30 of the columellate prosthesis 22 on the footplate. Again in this case, the changes to be made to the surgical procedure will be apparent to the surgeon expert in the sector.

The best sound transmission results are obtained by using that prosthetic device which employs a columellate prosthesis 22 the inner end 30 (FIG. 4) of which is inserted into the hole 32 formed in the footplate 24.

The reconstructions performed by columellate prosthesis resting on the stapes footplate or the stapes capitellum allow to obtain poorer sound transmission results. With respects to the present invention these two solutions can be considered surgical variants for particular needs (they being within the range of beginner surgeons).

It is important to note that because of the large distance between the wires 116A, 116B and 116D which form the tensostructure and because of the relative thinness of the various parts which form the Lorraine cross-shaped connection element 134, the surgeon has a good view of the underlying surgical field and there are no difficulties either in making the through hole in the footplate 24 with the laser, or in locating the columellate prosthesis 22 or 22A in the correct position.

It should also be noted that the connection between the neotympanum and the tensostructure 115, obtained using the prosthetic device of the present invention, prevents the neotympanum from becoming detached from the tensostructure 115 due to the retraction undergone by the neotympanum during the initial months after the intervention, so interrupting sound transmission.

It is still important to note that the connection element 134 carried by the tensostructure 115 vibrates in all directions in space (whereas in the prosthetic device of FIGS. 1-3 the elongated element 14 can vibrate only in the direction of its length), the columellate prosthesis 22 or 22A consequently vibrating independently of whether it is coupled to one or to the other of the two arms 144 of the longer crosspiece 136.

It is also important to note that the transmission of neotympanum vibrations to the columellate prosthesis 22 or 22A requires less energy than that required to cause the elongated element 14 of the prosthetic device of FIGS. 1-3 to vibrate (one end of this latter being fixed into the annular element 10).

The fact that the connection element 134 is carried by the tensostructure 115 enables the anatomy of the human ossicular chain to be essentially recreated.

The invention claimed is:

1. A middle ear prosthetic device, comprising:
   a columellate prosthesis arranged to replace, in sound wave transmission, an ossicular chain of the middle ear with the exception of the stapes footplate or the entire stapes, a first end of the columellate prosthesis being insertable into a hole provided in the footplate or arranged to rest on the footplate itself, or connectable to the stapes capitellum;
   an annular element of bioinert metal having an annular groove within which bone tissue is able to re-grow, the annular element being insertable into an outer auditory tube adjacent to a position at which a neotympanum is formable;
   a tensostructure of non-reabsorbable bioinert material, which extends into the interior of the annular element and is fixed to the annular element, the tensostructure presenting apertures which provide a surgeon with a sufficient view of a surgical field and allow the required surgical maneuvers;
   first means for connecting a second end of the columellate prosthesis to the tensostructure; and
   second means for connecting the neotympanum to the tensostructure.

2. The middle ear prosthetic device as claimed in claim 1, wherein the tensostructure is of a type comprising wires.

3. The middle ear prosthetic device as claimed in claim 2, wherein the wires are surgical wires of a non-reabsorbable bioinert polymer.

4. The middle ear prosthetic device as claimed in claim 1, wherein the first means comprise, connected to the tensostructure, a first arm to which the columellate prosthesis can be coupled, the second end of which is shaped as a hook.

5. The middle ear prosthetic device as claimed in claim 4, wherein the second means comprise a second arm connected to the tensostructure, this second arm being insertable into a hole provided in the neotympanum to connect the neotympanum to the tensostructure.

6. The middle ear prosthetic device as claimed in claim 5, wherein the first arm and the second arm both form part of a same connection element connected to the tensostructure.

7. The middle ear prosthetic device as claimed in claim 6, wherein the connection element has an overall Lorraine cross shape, the first arm forming one of the two arms of the longer crosspiece of the Lorraine cross, and the second arm forming the outer arm of a prone U-shaped element lying in a plane coaxial to the annular element and forming the upright of the Lorraine cross.

8. The middle ear prosthetic device as claimed in claim 7, wherein the first arm is covered with a sleeve of PTFE for medical use.

9. The middle ear prosthetic device as claimed in claim 7, wherein the shorter crosspiece of the Lorraine cross is provided with a hook at each of its two ends, the tensostructure being formed from two wire portions, each made to pass through the relative hook.

10. The middle ear prosthetic device as claimed in claim 2, wherein the ends of the wires are inserted into recesses-provided in the annular element, said ends being locked in the relative recesses by deforming the metal surrounding the recesses.

11. The middle ear prosthetic device as claimed in claim 7, wherein the inner arm of the U-shaped upright of the connection element is surrounded by a relative wire.

12. The middle ear prosthetic device as claimed in claim 7, wherein each of the two arms of the longer crosspiece of the connection element is surrounded by a relative wire.

13. The middle ear prosthetic device as claimed in claim 5, wherein the first arm and the second arm both form part of a same connection element connected to the tensostructure.

14. The middle ear prosthetic device as claimed in claim 13, wherein the connection element has an overall Lorraine cross shape, the first arm forming one of the two arms of the longer crosspiece of the Lorraine cross, and the second arm forming the outer arm of a prone U-shaped element lying in a plane coaxial to the annular element and forming the upright of the Lorraine cross.

15. The middle ear prosthetic device as claimed in claim 14, wherein the first arm is covered with a sleeve of PTFE for medical use.

16. The middle ear prosthetic device as claimed in claim 14, wherein the shorter crosspiece of the Lorraine cross is provided with a hook at each of its two ends, the tensostructure being formed from two wire portions, each made to pass through the relative hook.

17. The middle ear prosthetic device as claimed in claim 14, wherein the inner arm of the U-shaped upright of the connection element is surrounded by a relative wire.

18. The middle ear prosthetic device as claimed in claim 14, wherein each of the two arms of the longer crosspiece of the connection element is surrounded by a relative wire.

* * * * *